(12) United States Patent
Raikar et al.

(10) Patent No.: US 11,071,553 B2
(45) Date of Patent: Jul. 27, 2021

(54) ENDOSCOPIC SURGICAL CLIP APPLIER AND CLIP APPLYING SYSTEMS

(71) Applicant: Covidien LP, Mansfield, MA (US)

(72) Inventors: Anirudh Raikar, Shanghai (CN); Longsheng Cai, Shanghai (CN); Kun Zhao, Shanghai (CN); Yuandong Tan, Shanghai (CN)

(73) Assignee: COVIDIEN LP, Mansfield, MA (US)

( * ) Notice: Subject to any disclaimer, the term of this patent is extended or adjusted under 35 U.S.C. 154(b) by 287 days.

(21) Appl. No.: 16/308,874

(22) PCT Filed: Aug. 25, 2016

(86) PCT No.: PCT/CN2016/096666
§ 371 (c)(1),
(2) Date: Dec. 11, 2018

(87) PCT Pub. No.: WO2018/035796
PCT Pub. Date: Mar. 1, 2018

(65) Prior Publication Data
US 2020/0305883 A1 Oct. 1, 2020

(51) Int. Cl.
*A61B 17/128* (2006.01)
*A61B 17/00* (2006.01)

(52) U.S. Cl.
CPC .... *A61B 17/1285* (2013.01); *A61B 17/00234* (2013.01); *A61B 2017/00407* (2013.01); *A61B 2017/00464* (2013.01)

(58) Field of Classification Search
CPC .......... A61B 17/1285; A61B 17/00234; A61B 2017/00407; A61B 2017/00464;
(Continued)

(56) References Cited

U.S. PATENT DOCUMENTS

| 3,120,230 A | 2/1964 | Skold |
| 3,363,628 A | 1/1968 | Wood |

(Continued)

FOREIGN PATENT DOCUMENTS

| AU | 2013254887 A1 | 11/2013 |
| CA | 1163889 A | 3/1984 |

(Continued)

OTHER PUBLICATIONS

European Office Action corresponding to EP 12 152 989.5 dated May 4, 2015.

(Continued)

*Primary Examiner* — Shaun L David
*Assistant Examiner* — Joshua T Hicks

(57) ABSTRACT

An endoscopic surgical clip applier (10) includes a handle assembly (100) configured to releasably engage at least two in different endoscopic assemblies (200, 300). The handle assembly (100) is configured to transition from a non-ratcheting use condition to a ratcheting use condition when an endoscopic assembly (200) configured for ratcheting use is engaged with the handle assembly (100). The handle assembly (100) is maintained in the non-ratcheting use condition when an endoscopic assembly (300) configured for non-ratcheting use is engaged with the handle assembly (100). Endoscopic assemblies (200, 300) for use with the handle assembly (100) are also provided.

11 Claims, 11 Drawing Sheets

(58) Field of Classification Search
CPC ......... A61B 17/10; A61B 17/28; A61B 17/29; A61B 17/2909
See application file for complete search history.

(56) References Cited

U.S. PATENT DOCUMENTS

| | | |
|---|---|---|
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |

(56) References Cited

U.S. PATENT DOCUMENTS

| | | |
|---|---|---|
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |

(56) References Cited

U.S. PATENT DOCUMENTS

| | | |
|---|---|---|
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,632,270 B2 * | 12/2009 | Livneh .......... A61B 17/29 606/51 |
| 7,637,917 B2 | 12/2009 | Whitfield et al. |
| 7,644,848 B2 | 1/2010 | Swayze et al. |
| 7,686,820 B2 | 3/2010 | Huitema et al. |

(56) References Cited

U.S. PATENT DOCUMENTS

| | | |
|---|---|---|
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |
| 7,752,853 B2 | 7/2010 | Singh et al. |
| 7,753,250 B2 | 7/2010 | Clauson et al. |
| 7,766,207 B2 | 8/2010 | Mather et al. |
| 7,766,925 B2 | 8/2010 | Stokes et al. |
| 7,770,773 B2 | 8/2010 | Whitman et al. |
| 7,776,058 B2 | 8/2010 | Rosenberg et al. |
| 7,780,688 B2 | 8/2010 | Sakakine et al. |
| 7,793,813 B2 | 9/2010 | Bettuchi |
| 7,806,903 B2 | 10/2010 | Shibata et al. |
| 7,819,886 B2 | 10/2010 | Whitfield et al. |
| 7,823,592 B2 | 11/2010 | Bettuchi et al. |
| 7,857,828 B2 | 12/2010 | Jabba et al. |
| 7,871,416 B2 | 1/2011 | Phillips |
| 7,875,029 B1 | 1/2011 | Hausen |
| 7,887,553 B2 | 2/2011 | Lehman et al. |
| 7,887,554 B2 | 2/2011 | Stokes et al. |
| 7,892,244 B2 | 2/2011 | Monassevitch et al. |
| 7,896,895 B2 | 3/2011 | Boudreaux et al. |
| 7,901,420 B2 | 3/2011 | Dunn |
| 7,905,890 B2 | 3/2011 | Whitfield et al. |
| 7,914,544 B2 | 3/2011 | Nguyen et al. |
| 7,914,551 B2 | 3/2011 | Ortiz et al. |
| 7,942,890 B2 | 5/2011 | D'Agostino et al. |
| 7,947,052 B2 | 5/2011 | Baxter, III et al. |
| 7,954,682 B2 | 6/2011 | Giordano et al. |
| 7,963,433 B2 | 6/2011 | Whitman et al. |
| 7,967,831 B2 | 6/2011 | Rosenberg et al. |
| 7,988,027 B2 | 8/2011 | Olson et al. |
| 7,998,155 B2 | 8/2011 | Manzo |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,062,311 B2 | 11/2011 | Litscher et al. |
| 8,062,314 B2 | 11/2011 | Sixto, Jr. et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,074,857 B2 | 12/2011 | Peterson et al. |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,137,368 B2 | 3/2012 | Kayan et al. |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,177,797 B2 | 5/2012 | Shimoji et al. |
| 8,182,529 B2 | 5/2012 | Gordon et al. |
| 8,187,290 B2 | 5/2012 | Buckman et al. |
| 8,192,449 B2 | 6/2012 | Maier et al. |
| 8,211,119 B2 | 7/2012 | Palmer et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,241,322 B2 | 8/2012 | Whitman et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,287,559 B2 | 10/2012 | Barker et al. |
| 8,308,743 B2 | 11/2012 | Matsuno et al. |
| 8,313,497 B2 | 11/2012 | Walberg et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,545,519 B2 | 10/2013 | Aguirre et al. |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,716 B2 | 11/2013 | Roskopf et al. |
| 8,585,717 B2 | 11/2013 | Sorrentino et al. |
| 8,603,109 B2 | 12/2013 | Aranyi et al. |
| 8,623,044 B2 | 1/2014 | Timm et al. |
| 8,628,547 B2 | 1/2014 | Weller et al. |
| 8,632,520 B2 | 1/2014 | Otley |
| 8,636,191 B2 | 1/2014 | Meagher |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,210 B2 | 4/2014 | Zemlok et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,758,392 B2 | 6/2014 | Crainich |
| 8,771,169 B2 | 7/2014 | Whitman et al. |
| 8,795,302 B2 | 8/2014 | Wild |
| 8,808,310 B2 | 8/2014 | Jones et al. |
| 8,814,884 B2 | 8/2014 | Whitfield et al. |

(56) References Cited

U.S. PATENT DOCUMENTS

| | | |
|---|---|---|
| 8,821,516 B2 | 9/2014 | Huitema |
| 8,828,023 B2 | 9/2014 | Neff et al. |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santini et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020271 A1 | 1/2006 | Stewart et al. |
| 2006/0079912 A1 | 4/2006 | Whitfield et al. |
| 2006/0085015 A1 | 4/2006 | Whitfield et al. |
| 2006/0100649 A1 | 5/2006 | Hart |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0093856 A1 | 4/2007 | Whitfield et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |

(56) References Cited

U.S. PATENT DOCUMENTS

| | | |
|---|---|---|
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Lutze et al. |
| 2009/0088783 A1 | 4/2009 | Kennedy et al. |
| 2009/0182193 A1 | 7/2009 | Whitman et al. |
| 2009/0209946 A1 | 8/2009 | Swayze et al. |
| 2009/0228023 A1 | 9/2009 | Cui |
| 2009/0326558 A1 | 12/2009 | Cui et al. |
| 2010/0274264 A1 | 10/2010 | Schulz et al. |
| 2010/0318103 A1 | 12/2010 | Cheng et al. |
| 2011/0054498 A1 | 3/2011 | Monassevitch et al. |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0238044 A1* | 9/2011 | Main ............... A61B 17/2909 606/1 |
| 2011/0295290 A1 | 12/2011 | Whitfield |
| 2011/0313437 A1 | 12/2011 | Yeh |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2014/0074143 A1 | 3/2014 | Fitzgerald et al. |
| 2014/0263565 A1* | 9/2014 | Lytle, IV ............ A61B 17/072 227/180.1 |
| 2014/0276970 A1 | 9/2014 | Messerly et al. |
| 2014/0367448 A1* | 12/2014 | Cappola .............. A61B 17/068 227/177.1 |
| 2015/0032131 A1 | 1/2015 | Sorrentino et al. |
| 2016/0030044 A1 | 2/2016 | Zammataro |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0238936 A1 | 8/2017 | Mujawar |
| 2017/0258472 A1 | 9/2017 | Aranyi et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |

FOREIGN PATENT DOCUMENTS

| | | |
|---|---|---|
| CN | 1397256 A | 2/2003 |
| CN | 101507623 A | 8/2009 |
| CN | 103190939 A | 7/2013 |
| CN | 103565515 A | 2/2014 |
| CN | 104605911 B | 2/2017 |
| DE | 20 2005 001664 U1 | 5/2005 |
| DE | 202007003398 U1 | 6/2007 |
| DE | 202009006113 U1 | 7/2009 |
| EP | 0000756 A1 | 2/1979 |
| EP | 0406724 A1 | 1/1991 |
| EP | 0514139 A2 | 11/1992 |
| EP | 0732078 A2 | 9/1996 |
| EP | 0769275 A1 | 4/1997 |
| EP | 1769757 A1 | 4/2007 |
| GB | 2073022 A | 10/1981 |
| JP | 2002011019 A | 1/2002 |
| JP | 2003033361 A | 2/2003 |
| JP | 2006154230 A | 6/2006 |
| JP | 2006277221 A | 10/2006 |
| JP | 2008017876 A | 1/2008 |
| WO | 0042922 A1 | 7/2000 |
| WO | 0166001 A2 | 9/2001 |
| WO | 0167965 A1 | 9/2001 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |

OTHER PUBLICATIONS

Australian Office Action corresponding to AU 2009212759 dated May 7, 2015.
Chinese Office Action corresponding to Int'l Appln No. CN 201210212642.9 dated Jun. 3, 2015.
European Office Action corresponding to Int'l Appln No. EP 04 719 757.9 dated Jun. 12, 2015.
European Office Action corresponding to Int'l Appln No. EP 13 166 382.5 dated Jun. 19, 2015.
Japanese Office Action corresponding to Int'l Application No. JP 2010-226908 dated Jun. 26, 2015.
Extended European Search Report corresponding to Int'l Application No. EP 15 15 5024.1 dated Jul. 17, 2015.
Extended European Search Report corresponding to Int'l Application No. EP 14 19 2026.4 dated Jul. 17, 2015.

(56) References Cited

OTHER PUBLICATIONS

Japanese Office Action corresponding to Int'l Application No. JP 2011-160126 dated Aug. 10, 2015.
Extended European Search Report corresponding to Int'l Application No. EP 14 15 0321.9 dated Sep. 23, 2015.
Extended European Search Report corresponding to Int'l Application No. EP 11 25 0675.3 dated Oct. 7, 2015.
Extended European Search Report corresponding to Int'l Application No. EP 11 25 0674.6 dated Oct. 7, 2015.
Extended European Search Report corresponding to Int'l Application No. EP 12 19 3447.5 dated Oct. 19, 2015.
Canadian Office Action corresponding to Int'l Application No. CA 2,675,875 dated Oct. 26, 2015.
Japanese Office Action corresponding to Int'l Application No. JP 2015-005629 dated Oct. 28, 2015.
Japanese Office Action corresponding to Int3 1 Application No. JP 2014-245081 dated Oct. 28, 2015.
Canadian Office Action corresponding to Int'l Application No. CA 2,675,921 dated Oct. 30, 2015.
Chinese Office Action corresponding to Int'l Application No. CN 201210555570.8 dated Nov. 2, 2015.
Canadian Office Action corresponding to Int'l Application No. CA 2,676,309 dated Nov. 3, 2015.
Canadian Office Action corresponding to Int'l Application No. CA 2,676,211 dated Nov. 24, 2015.
Canadian Office Action corresponding to Int'l Application No. CA 2,676,547 dated Nov. 25, 2015.
Extended European Search Report corresponding to Int'l Application No. EP 15 17 3809.3 dated Nov. 25, 2015.
Chinese Office Action corresponding to Int'l Application No. CN 201210586814.9 dated Dec. 2, 2015.
Extended European Search Report corresponding to Int'l Application No. EP 12 17 2940.4 dated Dec. 14, 2015.
Chinese First Office Action corresponding to Int'l Appln. No. CN 201210586826.1 dated Dec. 30, 2015.
Extended European Search Report corresponding to Int'l Appln. No. EP 15 18 5362.9 dated Feb. 12, 2016.
Extended European Search Report corresponding to Int'l Appln. No. EP 12 19 7813.4 dated Mar. 7, 2016.
Canadian Office Action corresponding to Int'l Appln. No. CA 2,676,465 dated Mar. 8, 2016.
Japanese Office Action corresponding to Int'l Appln. No. JP 2014-245081 dated Mar. 18, 2016.
Japanese Office Action corresponding to Int'l Appln. No. JP 2015-005629 dated Mar. 18, 2016.
Extended European Search Report corresponding to Int'l Appln. No. EP 15 19 3549.1 dated Mar. 22, 2016.
International Search Report and Written Opinion corresponding to Int'l Appln. No. PCT/CN2015/082199 dated Mar. 31, 2016.
Extended European Search Report corresponding to Int'l Appln. No. EP 15 19 7251.0 dated Apr. 8, 2016.
Extended European Search Report corresponding to Int'l Appln. No. EP 16 15 0739.7 dated May 17, 2016.
Canadian Office Action corresponding to Int'l Appln. No. CA 2,716,672 dated May 31, 2016.
Canadian Office Action corresponding to Int'l Appln. No. CA 2,717,448 dated May 31, 2016.
Canadian Office Action corresponding to Int'l Appln. No. CA 2,721,951 dated Jun. 1, 2016.
Partial European Search Report corresponding to Int'l Appln. No. EP 16 15 0287.7 dated Jun. 16, 2016.
Chinese Second Office Action corresponding to Int'l Appln. No. CN 201210555570.8 dated Jun. 20, 2016.
Chinese First Office Action corresponding to Chinese Appln. No. CN 201410076318.8 dated Jan. 23, 2017.
Extended European Search Report corresponding to European Appln. No. EP 16 18 3184.7 dated Jan. 24, 2017.
Japanese Office Action corresponding to Japanese Appln. No. JP 2016-097807 dated Feb. 14, 2017.

European Office Action corresponding to European Appln. No. EP 12 19 3447.5 dated Apr. 4, 2017.
Chinese First Office Action corresponding to Chinese Appln. No. CN 201410008877.5 dated Apr. 6, 2017.
Extended European Search Report corresponding to European Appln. No. EP 17 15 3714.5 dated May 11, 2017.
Extended European Search Report corresponding to European Appln. No. EP 17 15 8519.3 dated May 19, 2017.
Extended European Search Report corresponding to European Appln. No. EP 17 15 7606.9 dated May 22, 2017.
European Office Action corresponding to European Appln. No. EP 11 25 0674.6 dated May 23, 2017.
Canadian Office Action corresponding to Canadian Appln. No. CA 2,743,402 dated May 30, 2017.
European Office Action corresponding to European Appln. No. EP 16 15 9324.9 dated Aug. 7, 2017.
Extended European Search Report issued in European Application No. 16913819.5 dated Mar. 19, 2020, 7 pages.
International Search Report for PCT/CN2016/096666 date of completion is May 5, 2017 (3 pages).
The extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).
The International Search Report corresponding to International Application No. PCT-US08-59859, completed Sep. 14, 2008; dated Sep. 18, 2008; (2 Pages).
The extended European Search Report corresponding to European Application No. EP 07 25 3807.7, completed Nov. 7, 2008; dated Nov. 26, 2008; (11 Pages).
The extended European Search Report corresponding to European Application No. EP 09 25 2049.3, completed Dec. 11, 2009; dated Jan. 12, 2010; (3 Pages).
The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).
The extended European Search Report corresponding to European Application No. EP 09 25 2052.7, completed Nov. 16, 2009; dated Nov. 24, 2009; (3 Pages).
The extended European Search Report corresponding to European Application No. EP 09 25 2053.5, completed Nov. 24, 2009; dated Dec. 1, 2009; (3 Pages).
The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 8, 2010; dated Feb. 5, 2010; (3 Pages).
The extended European Search Report corresponding to European Application No. EP 10 25 0497.4, completed May 4, 2010; dated May 12, 2010; (6 Pages).
The extended European Search Report corresponding to European Application No. EP 10 25 2079.8, completed Mar. 8, 2011; dated Mar. 17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).

(56) References Cited

OTHER PUBLICATIONS

The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).
The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 4, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745.7, completed Mar. 19, 2013 and dated Apr. 11, 2013; (8 Pages).
The Extended European Search Report corresponding to EP 12 15 2989.5, completed Apr. 9, 2013 and dated Apr. 18, 2013; (9 Pages).
The Extended European Search Report corresponding to EP 08 73 2820.9, completed Jul. 2, 2013 and dated Jul. 9, 2013; (10 Pages).
The Extended European Search Report corresponding to EP 13 17 2008.8, completed Aug. 14, 2013 and dated Aug. 28, 2013; (8 Pages).
The Extended European Search Report corresponding to EP 13 16 6382.5, completed Nov. 19, 2013 and dated Nov. 28, 2013; (8 Pages).
The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages).
The Extended European Search Report corresponding to EP 10 25 2112.7, completed Jul. 29, 2014 and dated Aug. 5, 2014; (8 pp).
The Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.

* cited by examiner

ENDOSCOPIC SURGICAL CLIP APPLIER AND CLIP APPLYING SYSTEMS

CROSS-REFERENCE TO RELATED APPLICATIONS

This application is a National Stage Application of PCT/CN2016/096666 under 35USC § 371 (a), the disclosure of the above-identified application is hereby incorporated by reference in its entirety.

BACKGROUND

Technical Field

The present disclosure relates to surgical clip appliers and clip applying systems. More particularly, the present disclosure relates to endoscopic surgical clip appliers having handle assemblies configured for use with various different endoscopic assemblies, and systems incorporating the same.

Description of Related Art

Endoscopic surgical clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures.

Endoscopic surgical clip appliers having various sizes (e.g., diameters), that are configured to apply a variety of diverse surgical clips, are also known in the art, and are capable of applying a single or multiple surgical clips during an entry to the body cavity. Such surgical clips are typically fabricated from a biocompatible material and are usually compressed over a vessel. Once applied to the vessel, the compressed surgical clip terminates the flow of fluid therethrough.

During endoscopic or laparoscopic procedures it may be desirable and/or necessary to use different size surgical clips or different configured surgical clips depending on the underlying tissue or vessels to be ligated. In order to reduce overall costs of an endoscopic surgical clip applier, it is desirable for a single endoscopic surgical clip applier capable of receiving and firing different size surgical clips as needed.

Accordingly, a need exists for endoscopic surgical clip appliers and systems that include handle assemblies configured for use with various different endoscopic assemblies having different clips loaded therein and/or configured for performing various different surgical tasks.

SUMMARY

As detailed herein and shown in the drawing figures, as is traditional when referring to relative positioning on a surgical instrument, the term "proximal" refers to the end of the apparatus or component thereof which is closer to the user and the term "distal" refers to the end of the apparatus or component thereof which is further away from the user. Further, to the extent consistent, any or all of the aspects and features detailed herein may be used in conjunction with any or all of the other aspects and features detailed herein.

Provided in accordance with an aspect of the present disclosure is a handle assembly of a surgical clip applier configured to releasably engage at least two different endoscopic assemblies. The handle assembly includes a housing defining a body portion and a fixed handle portion extending from the body portion. The trigger is pivotably connected to the housing and movable relative to the fixed handle portion between an un-actuated position and an actuated position. A drive bar is slidably supported within the body portion of the housing and operably coupled to the trigger such that movement of the trigger from the un-actuated position towards the actuated position translates the drive bar distally through the body portion of the housing. The drive bar includes a ratchet rack disposed thereon, and a ratchet mechanism is disposed within the body portion of the housing.

The ratchet mechanism includes a pawl pin, a ratchet pawl pivotably and slidably supported on the pawl pin, a biasing member, a cam arm, and a cam slider. The biasing member is positioned to bias the ratchet pawl along the pawl pin towards an off-set position relative to the ratchet rack, so that the ratchet pawl is inhibited from operably engaging the ratchet rack upon distal translation of the drive bar. The cam arm is pivotably and slidably supported on the pawl pin adjacent the ratchet pawl. The cam slider is selectively translatable through the body portion of the housing and relative to the cam arm between a first position, wherein the ratchet pawl is maintained in the off-set position under the bias of the biasing member, and a second position, wherein the cam slider urges the cam arm along the pawl pin to thereby urge the ratchet pawl along the pawl pin from the off-set position to an aligned position. In the aligned position, the ratchet pawl is aligned with the ratchet rack to permit operable engagement of the ratchet pawl with the ratchet rack upon distal translation of the drive bar.

The cam arm and the cam slider may define cam surfaces configured to cam along one another upon translation of the cam slider relative to the cam arm.

The cam slider may be operably engaged within a guide track defined on an interior surface of the body portion of the housing.

A cam slider biasing member may be configured to bias the cam slider towards the first position.

A pawl biasing member may be engaged between the ratchet pawl and the cam arm.

A latch assembly may be operably supported on the housing. The latch assembly may include a lever latch configured to releasably engage an endoscopic assembly inserted into the handle assembly.

The lever latch may include a distal engagement tooth configured to engage the endoscopic assembly inserted into the handle assembly.

The lever latch may include a proximal manipulation portion configured for manual manipulation to disengage the distal engagement tooth from the endoscopic assembly to permit removal of the endoscopic assembly from the handle assembly.

A surgical clip applying system provided in accordance with another aspect of the present disclosure includes a handle assembly and a first endoscopic assembly. The handle assembly includes a housing, a trigger pivotably connected to the housing and movable relative thereto between an un-actuated position and an actuated position. A drive bar is slidably supported within the housing and operably coupled to the trigger such that movement of the trigger from the un-actuated position towards the actuated position translates the drive bar distally through the housing. A ratchet mechanism is also disposed within the housing. The drive bar includes a ratchet rack disposed thereon.

The ratchet mechanism includes a pawl pin, a ratchet pawl pivotably and slidably supported on the pawl pin, a biasing member positioned to bias the ratchet pawl towards an off-set position relative to the ratchet rack, a cam arm, and a cam slider. In the off-set position, the ratchet pawl is inhibited from operably engaging the ratchet rack upon distal translation of the drive bar. The cam arm is supported on the pawl pin adjacent the ratchet pawl. The cam slider is selectively movable through the housing and relative to the cam arm. The cam slider is initially disposed in a first position, wherein the ratchet pawl is maintained in the off-set position under the bias of the biasing member. The first endoscopic assembly is configured for ratcheting use and includes a first proximal hub insertable into and releasably engagable within the housing.

Upon insertion of the first proximal hub into the housing, the cam slider is moved from the first position to a second position, so that the cam slider urges the cam arm along the pawl pin to thereby urge the ratchet pawl along the pawl pin from the off-set position to an aligned position. In the aligned position, the ratchet pawl is aligned with the ratchet rack to permit operable engagement of the ratchet pawl with the ratchet rack upon distal translation of the drive bar.

A second endoscopic assembly configured for non-ratcheting use may be provided. The second endoscopic assembly may include a second proximal hub insertable into and releasably engagable within the housing. Upon insertion of the second proximal hub into the housing, the cam slider may be maintained in the first position such that the ratchet pawl is maintained in the off-set position under the bias of the biasing member.

The first proximal hub may include a proximal extension configured to urge the cam slider from the first position to the second position upon insertion of the first proximal hub into the housing.

The second proximal hub may be devoid of a proximal extension such that, upon insertion of the second proximal hub into the housing, the cam slider is maintained in the first position and the ratchet pawl is maintained in the off-set position under the bias of the biasing member.

The handle assembly may further include a rotation knob extending distally from the housing and rotatably coupled to the housing. The rotation knob and the first proximal hub may define complementary indexing features to rotatably fix the first endoscopic assembly relative to the rotation knob upon insertion of the first proximal hub into the housing.

The handle assembly may further include a latch assembly operably supported on the housing. The latch assembly may include a lever latch configured to releasable engage the first proximal hub upon insertion of the first proximal hub into the housing.

The lever latch may include a distal engagement tooth and the first proximal hub may define an annular channel. The distal engagement tooth may be configured for engagement within the annular channel upon insertion of the first proximal hub into the housing.

The lever latch may include a proximal manipulation portion configured for manual manipulation to disengage the distal engagement tooth from the annular channel to permit removal of the first proximal hub from the housing.

Another surgical clip applying system provided in accordance with a further aspect of the present disclosure includes a handle assembly, a first endoscopic assembly, and a second endoscopic assembly. The handle assembly includes a housing and a drive bar configured to translate distally through the housing in response to actuation of the handle assembly. The drive bar includes a ratchet rack disposed thereon, and a ratchet mechanism is disposed within the housing.

The ratchet mechanism includes a pawl pin, a ratchet pawl pivotably and slidably supported on the pawl pin, a biasing member positioned to bias the ratchet pawl towards an off-set position relative to the ratchet rack, such that the ratchet pawl is inhibited from operably engaging the ratchet rack upon distal translation of the drive bar. A cam slider is longitudinally translatable relative to the housing. The cam slider is initially disposed in a first position, wherein the ratchet pawl is maintained in the off-set position under the bias of the biasing member. The first endoscopic assembly is configured for ratcheting use and is insertable into and releasably engagable within the housing.

Upon insertion of the first endoscopic assembly into the housing, the cam slider is translated from the first position to a second position, such that the cam slider urges the ratchet pawl along the pawl pin from the off-set position to an aligned position. In the aligned position, the ratchet pawl is aligned with the ratchet rack to permit operable engagement of the ratchet pawl with the ratchet rack upon distal translation of the drive bar. The second endoscopic assembly is configured for non-ratcheting use and is insertable into and releasably engagable within the housing. Upon insertion of the second endoscopic assembly into the housing, the cam slider is maintained in the first position such that the ratchet pawl is maintained in the off-set position under the bias of the biasing member.

The handle assembly may further include a latch assembly operably supported on the housing. The latch assembly may include a lever latch configured to releasably engage the first endoscopic assembly or the second endoscopic assembly upon insertion of the first endoscopic assembly or the second endoscopic assembly into the housing.

The first endoscopic assembly may include a first proximal hub defining a proximal extension configured to urge the cam slider from the first position to the second position upon insertion of the first proximal hub into the housing. The second endoscopic assembly may include a second proximal hub devoid of a proximal extension such that, upon insertion of the second proximal hub into the housing, the cam slider is maintained in the first position.

BRIEF DESCRIPTION OF THE DRAWINGS

Aspects and features of the presently-disclosed endoscopic surgical clip applier are described in detail with reference to the drawing figures wherein like reference numerals identify similar or identical structural elements and.

DETAILED DESCRIPTION

Figure 1:
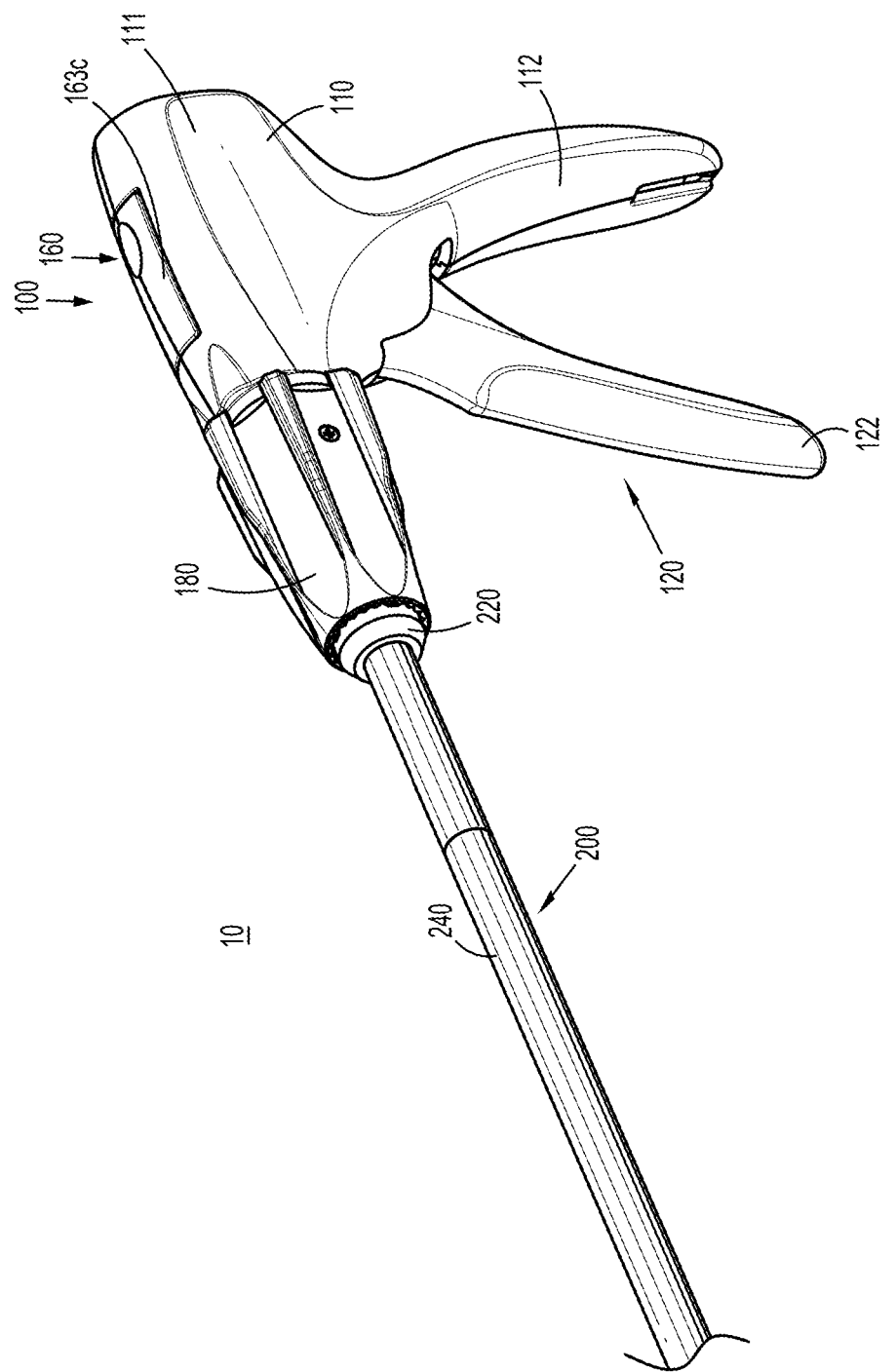
FIG. 1 is a front, perspective view of an endoscopic surgical clip applier provided in accordance with the present disclosure including a handle assembly having an endoscopic assembly engaged therewith.
Figure 2:
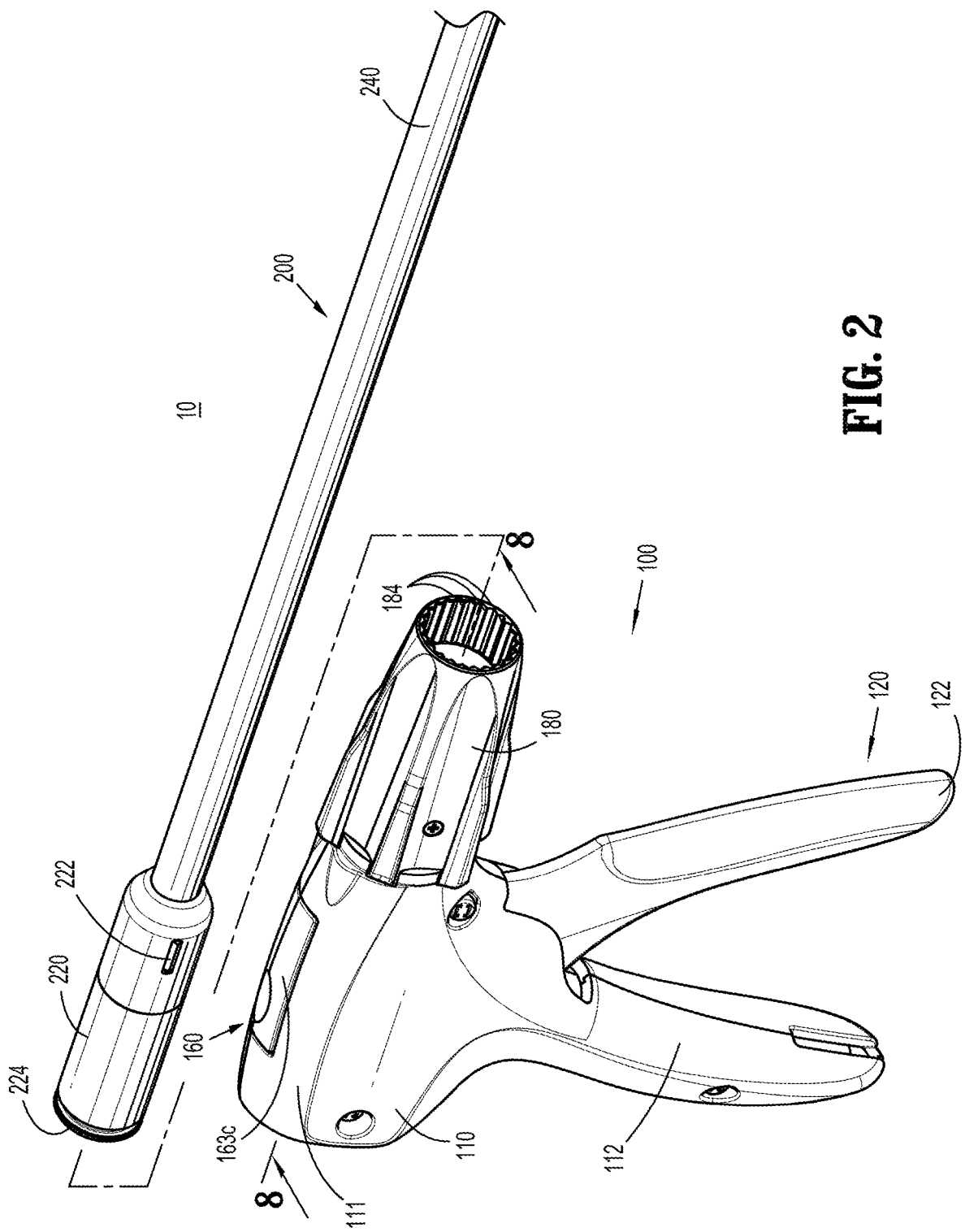
FIG. 2 is front, perspective view of the endoscopic surgical clip applier of FIG. 1 with the endoscopic assembly removed from the handle assembly.

Turning to FIGS. 1-2, an endoscopic surgical clip applier provided in accordance with the present disclosure is identified by reference numeral 10. Surgical clip applier 10 generally includes a handle assembly 100 and a plurality of endoscopic assemblies 200, 300 (FIGS. 3A and 3B) selectively connectable to handle assembly 100. Handle assembly 100 is configured to operate each of the plurality of endoscopic assemblies 200, 300 upon connection thereto, and may be configured as a sterilizable, reusable component such that handle assembly 100 may be repeatedly used with different and/or additional endoscopic assemblies 200, 300 during the course of one or more surgical procedures. The endoscopic assemblies 200, 300 may be configured as single-use disposable components, limited-use disposable components, or reusable components, depending upon a particular purpose and/or the configuration of the particular endoscopic assembly. In either configuration, the need for multiple handle assemblies 100 is obviated and, instead, the surgeon need only select an appropriate endoscopic assembly 200, 300 and connect that endoscopic assembly to handle assembly 100 in preparation for use.

Figure 2A:
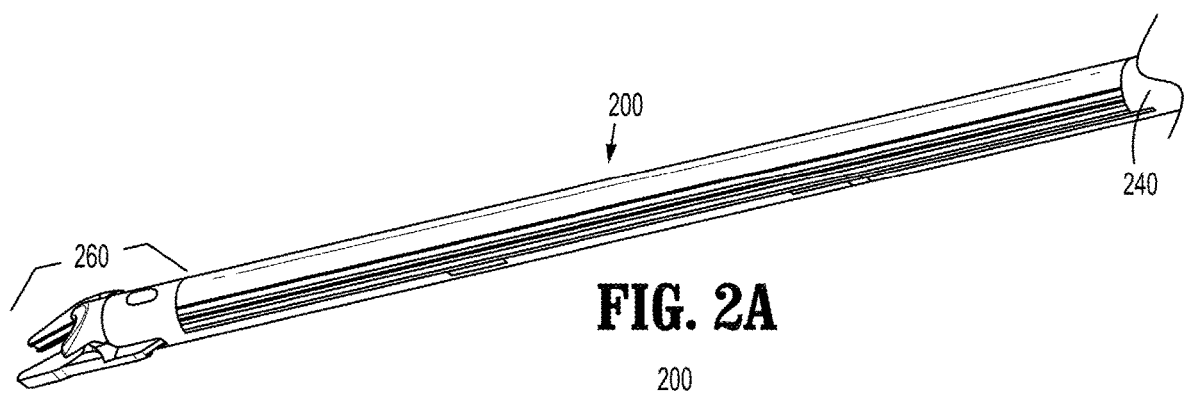
FIG. 2A is a side, perspective view of a distal end of the endoscopic assembly of FIGS. 1 and 2.
Figure 2B:
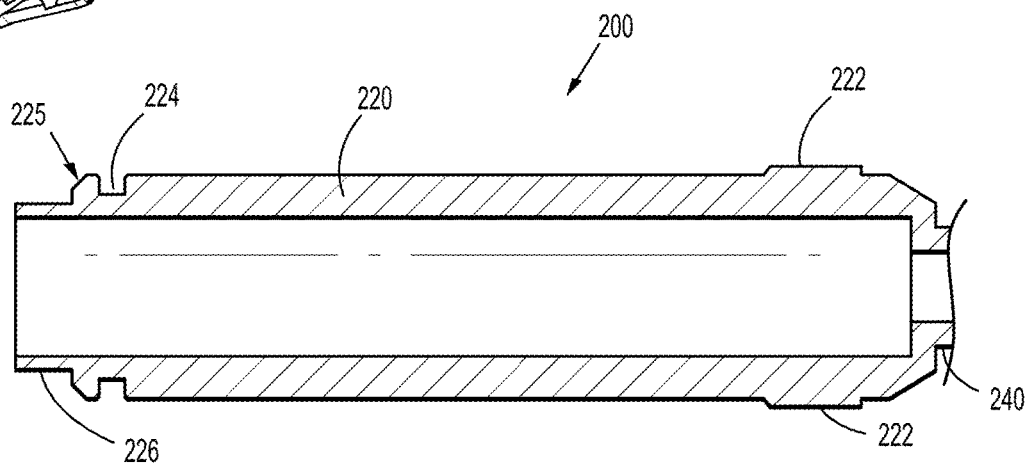
FIG. 2B is a side, longitudinal, cross-sectional view of a proximal portion of the outer shaft of the endoscopic assembly of FIGS. 1 and 2.
Figure 3A:
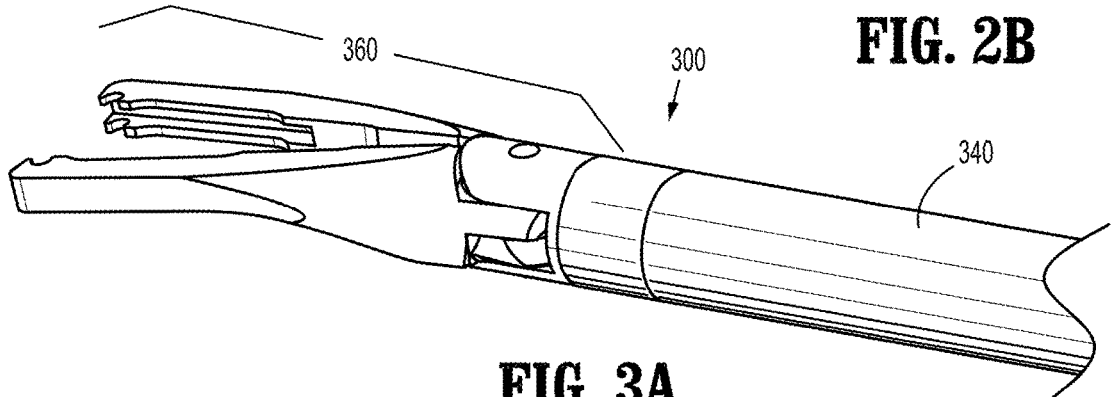
FIG. 3A is a side, perspective view of a distal end of another endoscopic assembly configured for use with the endoscopic clip applier of FIG. 1.
Figure 3B:
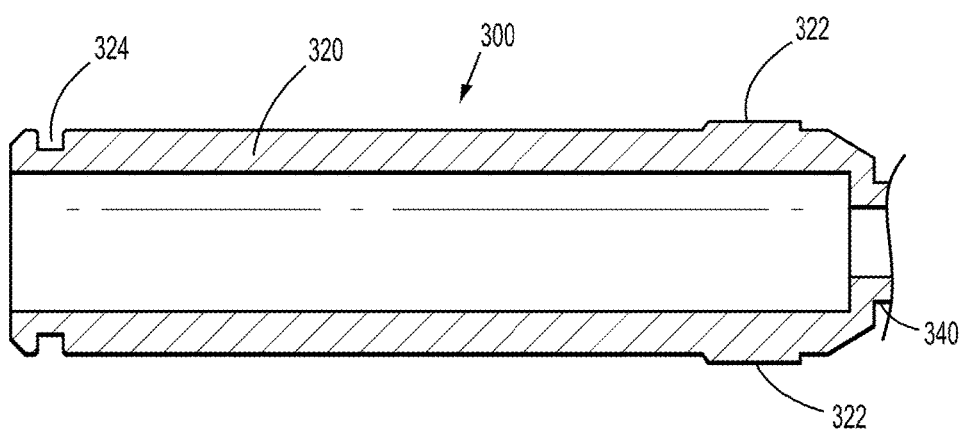
FIG. 3B is a side, longitudinal, cross-sectional view of a proximal portion of the outer shaft of the endoscopic assembly of FIG. 3A.

With additional reference to FIGS. 2A-3B, handle assembly 100, more specifically, is configured for both ratcheting use, e.g., in connection with endoscopic assembly 200 (FIGS. 1, 2, and 2A-2B), and non-ratcheting use, e.g., in connection with endoscopic assembly 300 (FIGS. 3A and 3B). Referring to FIGS. 2, 2A, and 2B, endoscopic assembly 200 is configured for ratcheting use and generally includes a proximal hub 220, an elongated shaft 240 extending distally from proximal hub 220, an end effector assembly 260 disposed towards a distal end portion of elongated shaft 240, and an inner drive assembly (not shown) operably coupled between handle assembly 100 and end effector assembly 260 when endoscopic assembly 200 is engaged with handle assembly 100 to enable the sequential firing and forming of at least one surgical clip (not shown) about tissue. Proximal hub 220 defines a plurality of indexing protrusions 222 annularly disposed thereabout towards a distal end portion thereof, an annular channel 224 defined therein towards a proximal end portion thereof, and a proximal tube extension 226 extending proximally from proximal hub 220. These features of proximal hub 220 are described in greater detail below. A more-detailed description of end effector assembly 260 and the inner drive assembly (not shown) of endoscopic assembly 200 are provided in International Application No. PCT/CN2015/091603, filed on Oct. 10, 2015, the entire content of which is hereby incorporated herein by reference. Further, it is contemplated that endoscopic assembly 200 may be configured to close, fire or form surgical clips similar to those shown and described in U.S. Pat. No. 7,819,886 or 7,905,890, the entire content of each of which is incorporated herein by reference.

Referring to FIGS. 3A-3B, endoscopic assembly 300 is configured for non-ratcheting use and generally includes a proximal hub 320, an elongated shaft 340 extending distally from proximal hub 320, an end effector assembly 360 disposed towards a distal end portion of elongated shaft 340, and an inner drive assembly (not shown) operably coupled between handle assembly 100 and end effector assembly 360 when endoscopic assembly 300 is engaged with handle assembly 100 to enable grasping and/or manipulation of tissue, retrieval of a surgical clip, and firing and forming the surgical clip about tissue. Proximal hub 320 defines a plurality of indexing protrusions 322 annularly disposed thereabout towards a distal end portion thereof and an annular channel 324 defined therein towards a proximal end portion thereof. Notably, and in contrast to proximal hub 220 of endoscopic assembly 200 (FIG. 2B), the proximal end of proximal hub 320 defines the proximal-most portion of proximal hub 320; proximal hub 320 does not include a proximal tube extension extending therefrom. A more-detailed description of end effector assembly 360 and the inner drive assembly (not shown) of endoscopic assembly 300 are also provided in International Application No. PCT/CN2015/091603, previously incorporated herein by reference. It is contemplated that endoscopic assembly 300 may be configured to close, fire or form surgical clips similar to those shown and described in U.S. Pat. No. 4,834,096, the entire content of which is incorporated herein by reference.

Although exemplary endoscopic assemblies 200, 300 configured for ratcheting and non-ratcheting use, respectively, are detailed above, it is contemplated that various other endoscopic assemblies for performing various different surgical tasks and/or having various different configurations suitable for ratcheting or non-ratcheting use may likewise be utilized with handle assembly 100. More specifically, it is contemplated and within the scope of the present disclosure that other endoscopic assemblies including a pair of jaws having a unique and diverse closure stroke length may be provided for use with handle assembly 100 for ratcheting use or non-ratcheting use, in a similar manner as detailed above with respect to endoscopic assemblies 200, 300. Such a configuration accommodates various different endoscopic assemblies having different configurations and/or different closure stroke lengths, while providing a constant actuation stroke length of trigger 122 of trigger assembly 120 of handle assembly 100. Accordingly, various endoscopic assemblies, constructed in accordance with the principles of the present disclosure, may be provided which are also capable of firing or forming or closing surgical clips of various sizes, materials, and configurations, across multiple platforms for multiple different manufactures.

Figure 4:
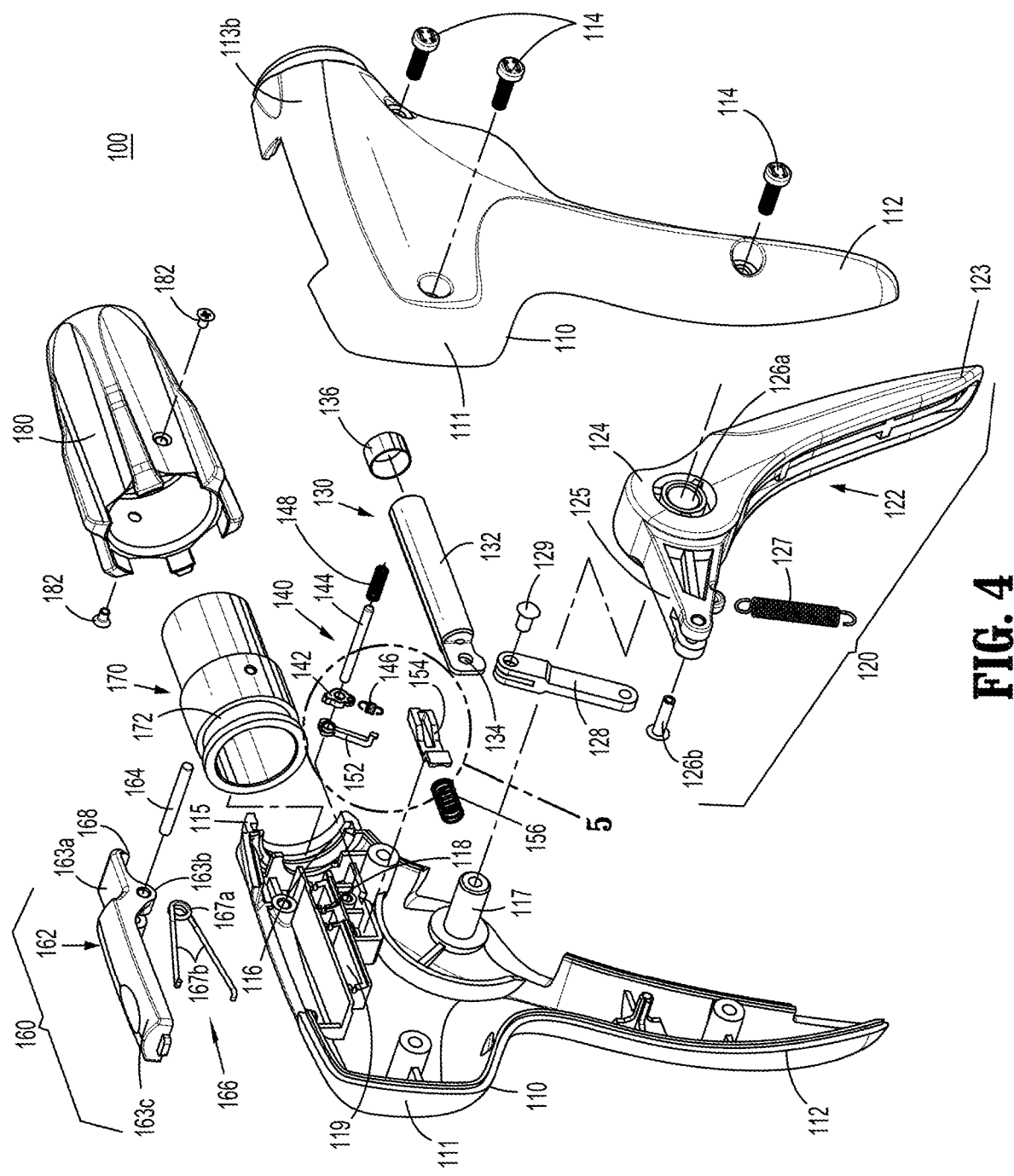
FIG. 4 is a rear, perspective, exploded view of the handle assembly of FIG. 1.

With reference to FIGS. 1, 2, and 4, handle assembly 100 generally includes a housing 110, a trigger assembly 120 pivotably coupled to housing 110, a drive assembly 130 operably coupled to trigger assembly 120, a ratchet mechanism 140 selectively operably associated with drive assembly 130, a latch assembly 160 configured to releasably latch an endoscopic assembly 200, 300 (FIGS. 2-2B and 3A-3B, respectively) in engagement with handle assembly 100, a receiver tube 170 extending distally from housing 110 and configured to receive the proximal hub 220, 320 of the endoscopic assembly 200, 300 (FIGS. 2-2B and 3A-3B, respectively) inserted into handle assembly 100, and a rotation knob 180 disposed about receiver tube 170. Handle assembly 100 is detailed below in connection with endoscopic assembly 200. Similarities in the engagement and use of handle assembly 100 with a non-ratcheting endoscopic assembly, e.g., endoscopic assembly 300 (FIGS. 3A and 3B), and with ratcheting endoscopic assembly 200 will not be described in detail below for purposes of brevity. Differences therebetween will be noted hereinbelow where applicable.

Housing 110 of handle assembly 100 defines a body portion 111 and a fixed handle portion 112 extending downwardly from body portion 111. Housing 110 is formed from first and second housing components or halves 113a, 113b secured to one another via a plurality of screws 114, although first and second housing components 113a, 113b may alternatively be secured in any other suitable manner, e.g., ultrasonic welding, gluing, other mechanical engagement, etc. Housing 110 is configured to house the internal working components of handle assembly 100. Body portion 111 includes a distal nose 115 defining an annular slot 116 on the interior thereof. More specifically, first and second housing components 113a, 113b each define a semi-annular slot portion such that, when first and second housing components 113a, 113b cooperate to form housing 110, annular slot 116 is formed. Receiver tube 170 of handle assembly 100 includes an annular rim 172 disposed thereabout towards a proximal end portion thereof. Annular rim 172 is captured within annular slot 116 defined within distal nose 115 of housing 110, e.g., upon engagement of first and second housing components 113a, 113b with one another. Annular rim 172 is captured within annular slot 116 to rotatably engage receiver tube 170 with housing 110. Rotation knob 180 of handle assembly 100 is engaged about receiver tube 170, e.g., via a pair of opposed engagement pins 182, in fixed rotational orientation relative thereto such that rotation of rotation knob 180 relative to housing 110 effects similar rotation of receiver tube 170 relative to housing 110.

Body portion 111 of housing 110 further includes an internal pivot post 117 (FIGS. 4 and 8) extending transversely between housing components 113a, 113b (from either or both of housing components 113a, 113b) and a pivot aperture 118 defined within each of housing components 113a, 113b. Fixed handle portion 112 of housing 110 is configured to facilitate grasping of handle assembly 100 and manipulation thereof and is monolithically formed with body portion 111, although other configurations are also contemplated.

Continuing with reference to FIGS. 1, 2, and 4, trigger assembly 120 generally includes a trigger 122, a biasing member 127, and a linkage 128. Trigger 122 includes a grasping portion 123, an intermediate pivot portion 124, and a proximal extension portion 125. Grasping portion 123 of trigger 122 extends downwardly from body portion 111 of housing 110 in opposed relation relative to fixed handle portion 112 of housing 110. Grasping portion 123 is configured to facilitate grasping and manipulation of trigger 122. Intermediate pivot portion 124 of trigger 122 is at least partially disposed within housing 110 and defines a pivot aperture 126a that is configured to receive pivot post 117 of housing 110 so as to enable pivoting of trigger 122 about pivot post 117 and relative to housing 110, e.g., between an un-actuated position, wherein grasping portion 123 of trigger 122 is spaced-apart relative to fixed handle portion 112, and an actuated position, wherein grasping portion 123 of trigger 122 is approximated relative to fixed handle portion 112.

Proximal extension portion 125 of trigger 122 of trigger assembly 120 is disposed on an opposite side of intermediate pivot portion 124 and, thus, pivot post 117, as compared to grasping portion 123 of trigger 122. As such, pivoting of grasping portion 123 proximally, e.g., towards the actuated position, urges proximal extension portion 125 distally. Proximal extension portion 125 is pivotably coupled to the proximal end of linkage 128 via a first pin 126b. Biasing member 127 is secured at either end and extends between proximal extension portion 125 and a support disposed within fixed handle portion 112 of housing 110. Pivoting of the grasping portion 123 towards the actuated position elongates biasing member 127 storing energy therein such that, upon release of grasping portion 123, grasping portion 123 is returned towards the un-actuated position under the bias of biasing member 127. Although illustrated as an extension coil spring, biasing member 127 may define any suitable configuration for biasing grasping portion 123 of trigger 122 towards the un-actuated position.

As noted above, linkage 128 is coupled at its proximal end to proximal extension portion 125 of trigger 122 via first pin 126b. Linkage 128 is also pivotably coupled at its distal end via a second pin 129, to proximal extension 134, which extends distally from drive bar 132 of drive assembly 130. As a result of this configuration, pivoting of grasping portion 123 of trigger 122 towards the actuated position urges proximal extension portion 125 of trigger 122 distally which, in turn, urges linkage 128 distally.

Figure 8:
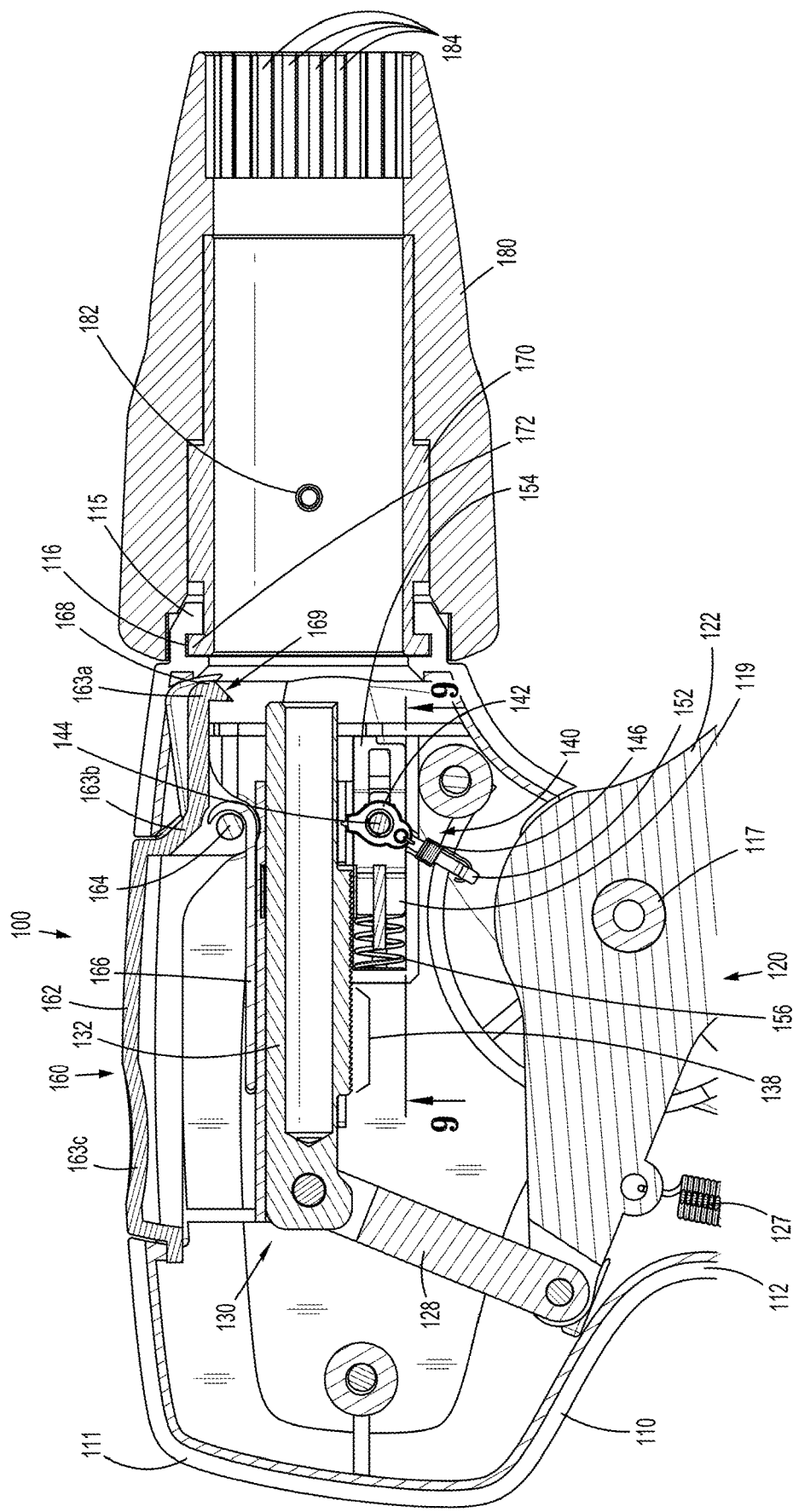
FIG. 8 is a side, longitudinal, cross-sectional view taken across section line "8-8" in FIG. 2.
Figure 9:
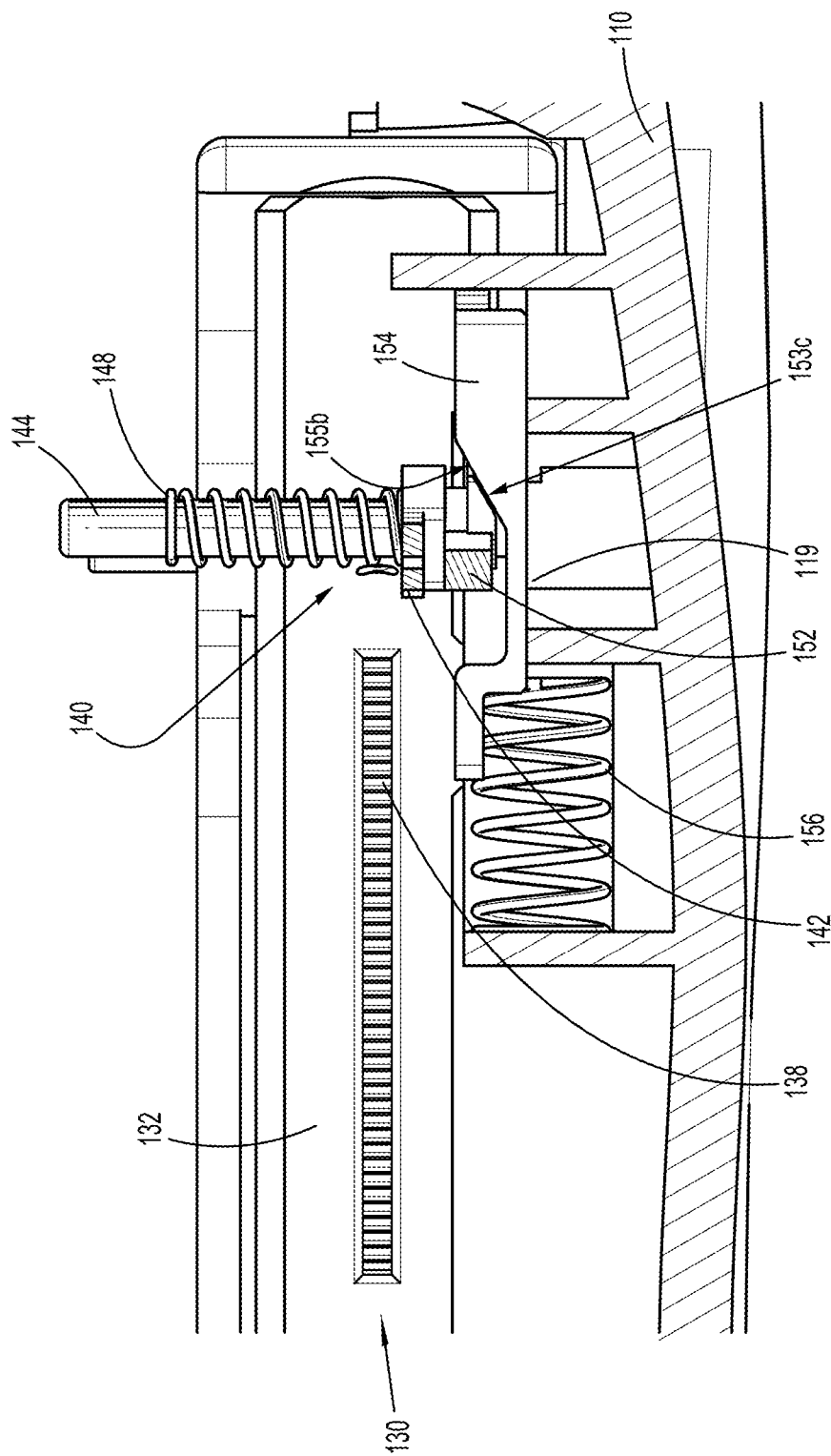
FIG. 9 is a bottom, longitudinal, cross-sectional view taken across section line "9-9" in FIG. 8.

Drive assembly 130 of handle assembly 100 includes drive bar 132, proximal extension 134, a support collar 136, and a ratchet rack 138 (FIGS. 4, 8 and 9). Drive bar 132 extends in a generally longitudinal direction. As noted above, proximal extension 134 extends proximally from drive bar 132 and receives second pin 129 to pivotably couple drive bar 132 with linkage 128. Support collar 136 is slidably disposed about drive bar 132 and fixed within housing 110. Support collar 136 serves to confine drive bar 132 to longitudinal translation relative to housing 110. Ratchet rack 138 extends in a generally longitudinal direction, similar to drive bar 132, and is defined on or engaged with drive bar 132 on an underside thereof.

Figure 6:
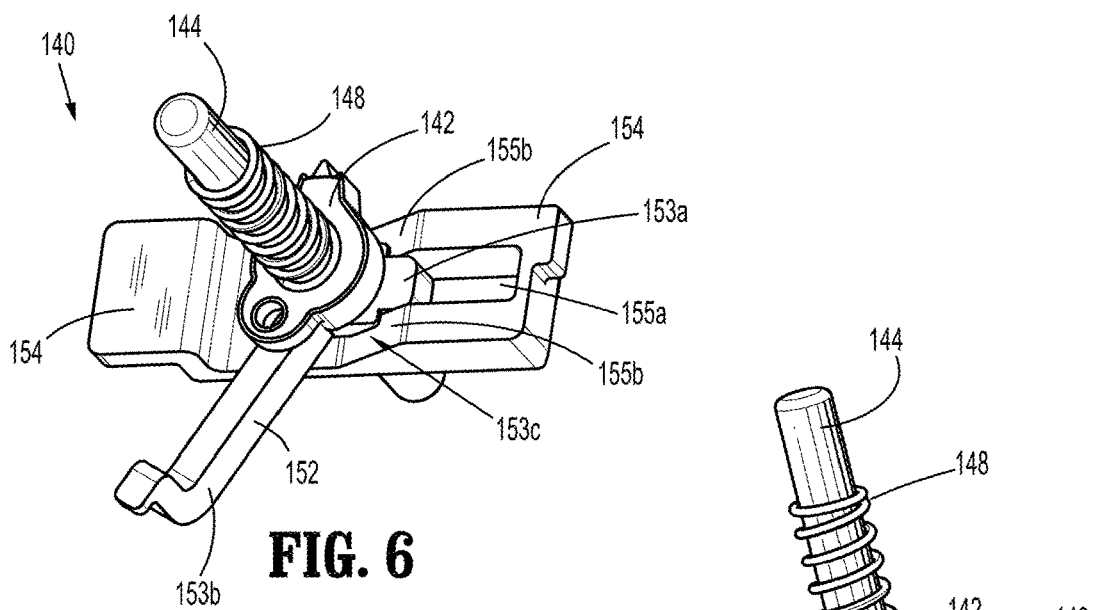
FIG. 6 is a perspective view of the ratchet mechanism of the handle assembly of FIG. 1.
Figure 7:
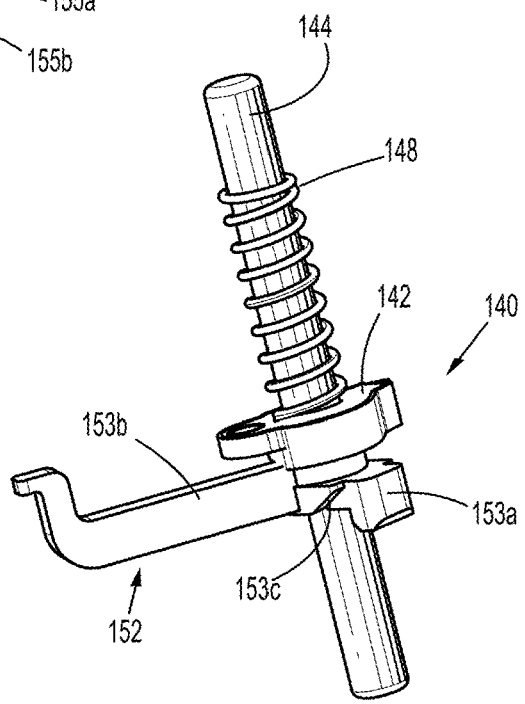
FIG. 7 is another perspective view of the ratchet mechanism of FIG. 6 with portions removed.

Referring to FIGS. 6 and 8, ratchet mechanism 140 of handle assembly 100, as noted above, is selectively operably associated with drive assembly 130 to enable use of handle assembly 100 in either a ratcheting condition or a non-ratcheting condition. Ratchet mechanism 140 includes a ratchet pawl 142, a pawl pin 144, a pawl biasing member 146, a transverse biasing member 148, a cam arm 152, a cam slider 154, and a cam slider biasing member 156.

Ratchet pawl 142 is pivotably disposed about pawl pin 144, which extends transversely between housing components 113a, 113b of housing 110 and is received within pivot apertures 118 of housing components 113a, 113b. Ratchet pawl 142 is also transversely slidable about pawl pin 144 and relative to drive assembly 130. Transverse biasing member 148 biases ratchet pawl 142 towards an off-set position relative to ratchet rack 138 of drive assembly 130 to inhibit operable engagement therebetween. Transverse biasing member 148 may be configured as a coil compression spring, although other configurations are also contemplated. This biased, off-set position of ratchet pawl 142 corresponds to the non-ratcheting use condition of ratchet mechanism 140 (see FIG. 9). As detailed below, in response to engagement of an endoscopic assembly configured for ratcheting use, e.g., endoscopic assembly 200 (FIGS. 2, 2A, and 2B) with handle assembly 100, ratchet pawl 142 is transversely slid, against the bias of transverse biasing member 148, to an aligned position relative to ratchet rack 138, corresponding to the ratcheting use condition of ratchet mechanism 140.

Figure 5:
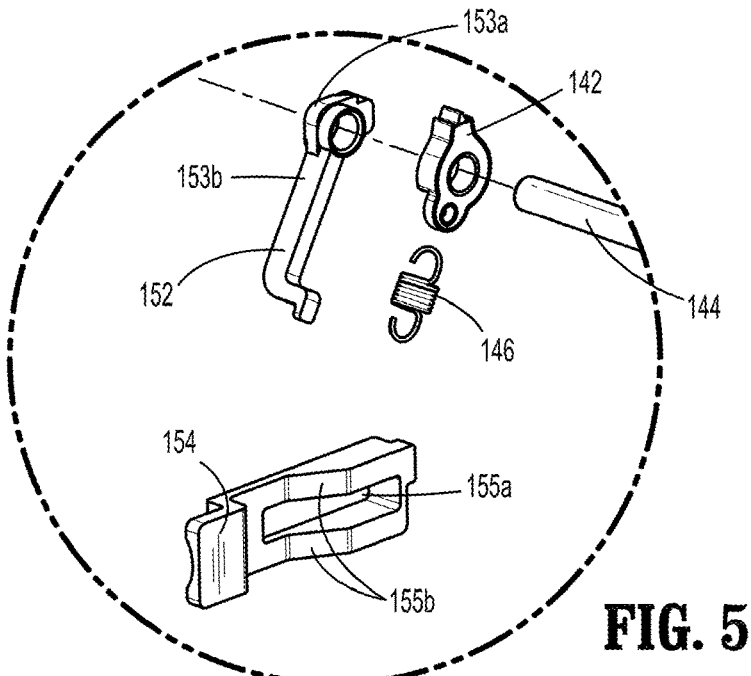
FIG. 5 is an enlarged perspective view of the area of detail indicated as "5" in FIG. 4.

Cam arm 152 of ratchet mechanism 140 is disposed about pawl pin 144 adjacent ratchet pawl 142. More specifically, cam arm 152 includes a base 153a disposed about pawl pin 144 and an extension 153b that extends from pawl pin 144. Base 153a of cam arm 152 is slidably received, in fixed rotational orientation, within a slot 155a defined within cam slider 154 and defines a pair of angled cam surfaces 153c. Extension 153b extends from base 153a to a free end of cam arm 152. Pawl biasing member 146 (FIG. 5) is coupled to and disposed between the free end of cam arm 152 and ratchet pawl 142 so as to bias ratchet pawl 142 towards an operable orientation relative to ratchet rack 138 of drive assembly 130. Pawl biasing member 142 may be configured as a coil extension spring, although other configurations are also contemplated Cam slider 154 is slidably received within a longitudinally-extending guide track 119 defined within housing component 113a of housing 110 of handle assembly 100 (although guide track 119 may alternatively be defined within housing component 113b of housing 110 of handle assembly 100) to confine cam slider 154 to longitudinal translation within and relative to housing 110. Cam slider 154, as noted above, defines a slot 155a that slidably receives base 153a of cam arm 152. Cam slider 154 further defines a pair of angled cam surfaces 155b that are angled oppositely relative to and disposed in abutment with angled cam surfaces 153c of base 153a of cam arm 152. The abutting pairs of angled cam surfaces 153c, 155b are relatively oriented such that proximal translation of cam slider 154 relative to cam arm 152 urges cam arm 152 transversely along pawl pin 144 towards ratchet pawl 142 to similarly urge ratchet pawl 142 transversely along pawl pin 144 from the off-set position (FIG. 9) towards the aligned position (FIG. 12) against the bias of transverse biasing member 148. Return of cam slider 154 distally permits ratchet pawl 142 and, thus, cam arm 152, to return transversely towards the off-set position under the bias of transverse biasing member 148.

Cam slider biasing member 156 is retained within guide track 119 of housing component 113a, positioned to bias cam slider 154 distally, and may be configured as a coil compression spring (although other configurations are also contemplated). As such, in the absence of other influence, cam slider 154 is biased towards a distal-most position and, accordingly, ratchet pawl 142 is biased towards the off-set position (FIG. 9). In the off-set position of ratchet pawl 142, corresponding to the non-ratcheting use condition of handle assembly 100, ratchet pawl 142 is inhibited from operably engaging ratchet rack 138 upon distal advancement of drive bar 132 (see FIG. 9). On the other hand, in the aligned position of ratchet pawl 142, corresponding to the ratcheting use condition of handle assembly, 100, ratchet pawl 142 is positioned to operably engage ratchet rack 138 upon distal advancement of drive bar 132 (see FIG. 12).

Figure 10:
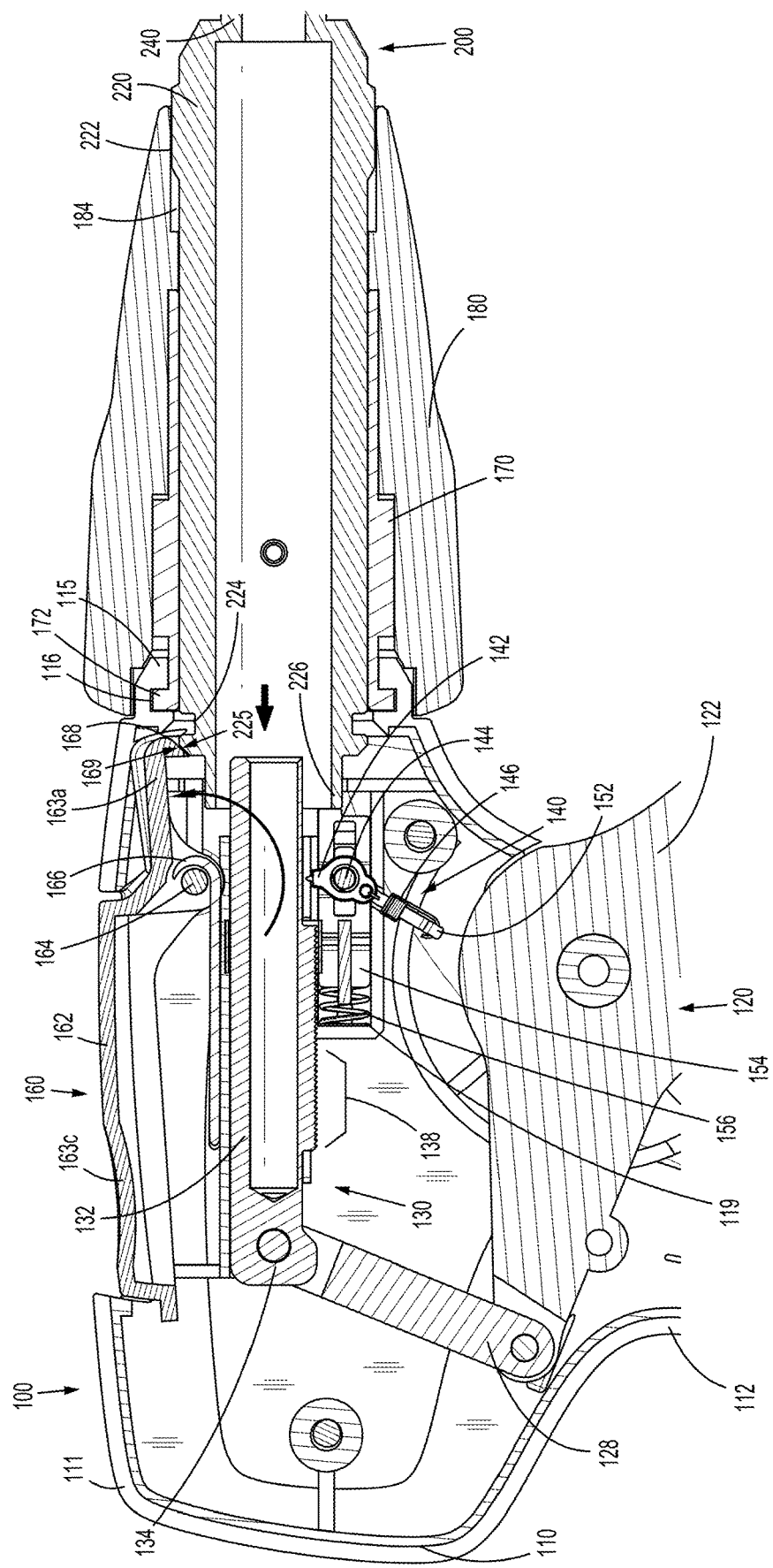
FIGS. 10 and 11 are side, longitudinal, cross-sectional views of the handle assembly of FIG. 1 illustrating engagement of the endoscopic assembly of FIGS. 1 and 2 within the handle assembly of FIGS. 1 and 2.
Figure 11:
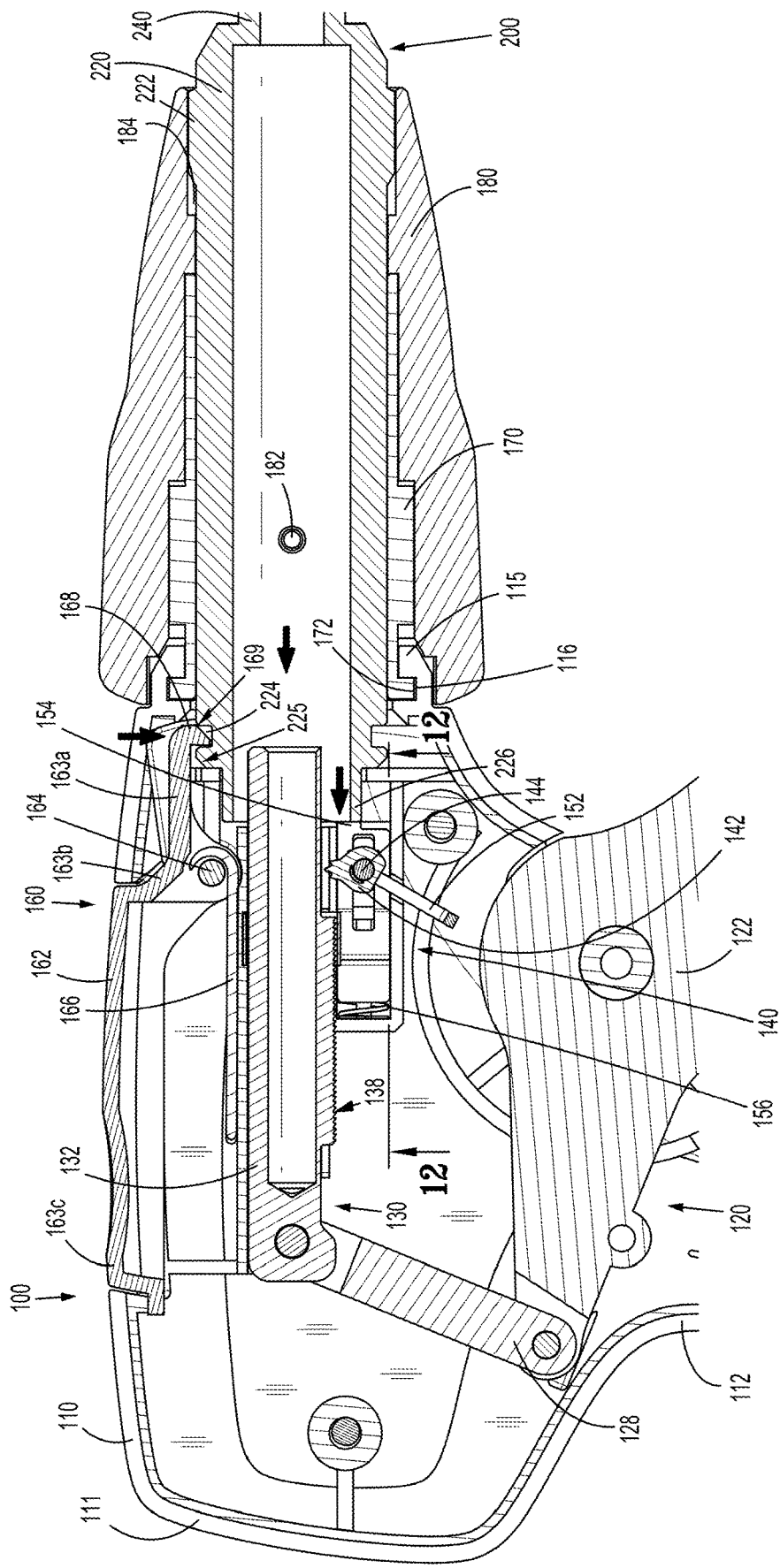

With reference to FIGS. 8, 10, and 11, latch assembly 160 includes a latch lever 162, a pivot pin 164, and a biasing member 166. Latch lever 162 is at least partially disposed within a cut-out defined without housing 110 of handle assembly 100 to enable manual manipulation thereof and defines a distal engagement section 163a, an intermediate section 163b, and a proximal manipulatable section 163c. Distal engagement section 163a of latch lever 162 includes an engagement tooth 168 extending therefrom. Engagement tooth 168 is configured to engage an endoscopic assembly, e.g., endoscopic assembly 200, inserted into handle assembly 100. With respect to endoscopic assembly 200, for example, upon insertion of proximal hub 220 of endoscopic assembly 200 into handle assembly 100, engagement tooth 168 is configured to cam over the proximal end of proximal hub 220 and into engagement within annular channel 224 to thereby lock endoscopic assembly 200 in engagement with handle assembly 100. To this end, engagement tooth 168 defines a cam surface 169 configured to interact with a corresponding cam surface 225 defined towards a proximal end portion of proximal hub 220 of endoscopic assembly 200 to facilitate camming of engagement tooth 168 over the proximal end of proximal hub 220 and into engagement within annular channel 224.

Pivot pin 164 of latch assembly 160 pivotably couples intermediate section 163b of lever latch 162 with housing 110 of handle assembly 100 such that urging of proximal manipulation section 163c of lever latch 162 in a first direction into housing 110, urges distal engagement section 163a of lever latch 162 in a second, opposite direction out of engagement with annular channel 224 of proximal hub 220 of endoscopic assembly 200. Biasing member 166 is configured as a torsion spring having a body 167a disposed about pivot pin 164 and first and second legs 167b disposed between housing 110 and proximal manipulation section 163c of lever latch 162 to bias proximal manipulation section 163c of lever latch 162, thereby biasing distal engagement section 163a towards an engaged position. However, other suitable configurations of biasing member 166 are also contemplated. Proximal manipulation section 163c of lever latch 162 is selectively depressible, against the bias of biasing member 166, to urge distal engagement section 163a towards a disengaged position.

Referring to FIG. 8, receiver tube 170 of handle assembly 100, as noted above, includes annular rim 172 captured within annular slot 116 defined within distal nose 115 of housing 110 to rotatably engage receiver tube 170 within housing 110. Rotation knob 180 of handle assembly 100, as also noted above, is engaged about receiver tube 170 via a pair of opposed engagement pins 182. Rotation knob 180 further defines a plurality of longitudinally-extending grooves 184 arranged annularly on an interior surface thereof. Grooves 184 are configured to slidably receive indexing protrusions 222 of proximal hub 220 of endoscopic assembly 200 to rotationally fix proximal hub 220 of endoscopic assembly 200 relative to rotation knob 180 upon insertion of proximal hub 220 into handle assembly 100. As such, in use, rotation of rotation knob 180 effects corresponding rotation of endoscopic assembly 200.

FIGS. 8-13, show the various stages of insertion and engagement of endoscopic assembly 200 with handle assembly 100. Initially, prior to insertion of endoscopic assembly 200, as illustrated in FIGS. 8 and 9, trigger 122 is disposed in the un-actuated position under the bias of biasing member 127, drive bar 132 is disposed in a proximal-most position, ratchet pawl 142 is disposed in the off-set position under the bias of transverse biasing member 148, and lever latch 162 disposed in the engaged position under the bias of biasing member 166.

In order to engage endoscopic assembly 200 with handle assembly 100, proximal hub 220 of endoscopic assembly 200 is inserted into rotation knob 180 of handle assembly 100 such that indexing protrusions 222 of proximal hub 220 are slidably received within longitudinally-extending grooves 184 of rotation knob 180. Thereafter, as illustrated in FIG. 10, proximal hub 220 is slid proximally through rotation knob 180, receiver tube 170, and into housing 110. As proximal hub 220 enters housing 110, proximal hub 220 receives the distal end of drive bar 132; engagement tooth 168 of latch assembly 160 begins to cam over the proximal end of proximal hub 220; and proximal tube extension 226 of endoscopic assembly 200 is translated into contact with cam slider 154 of ratchet mechanism 140.

Figure 12:
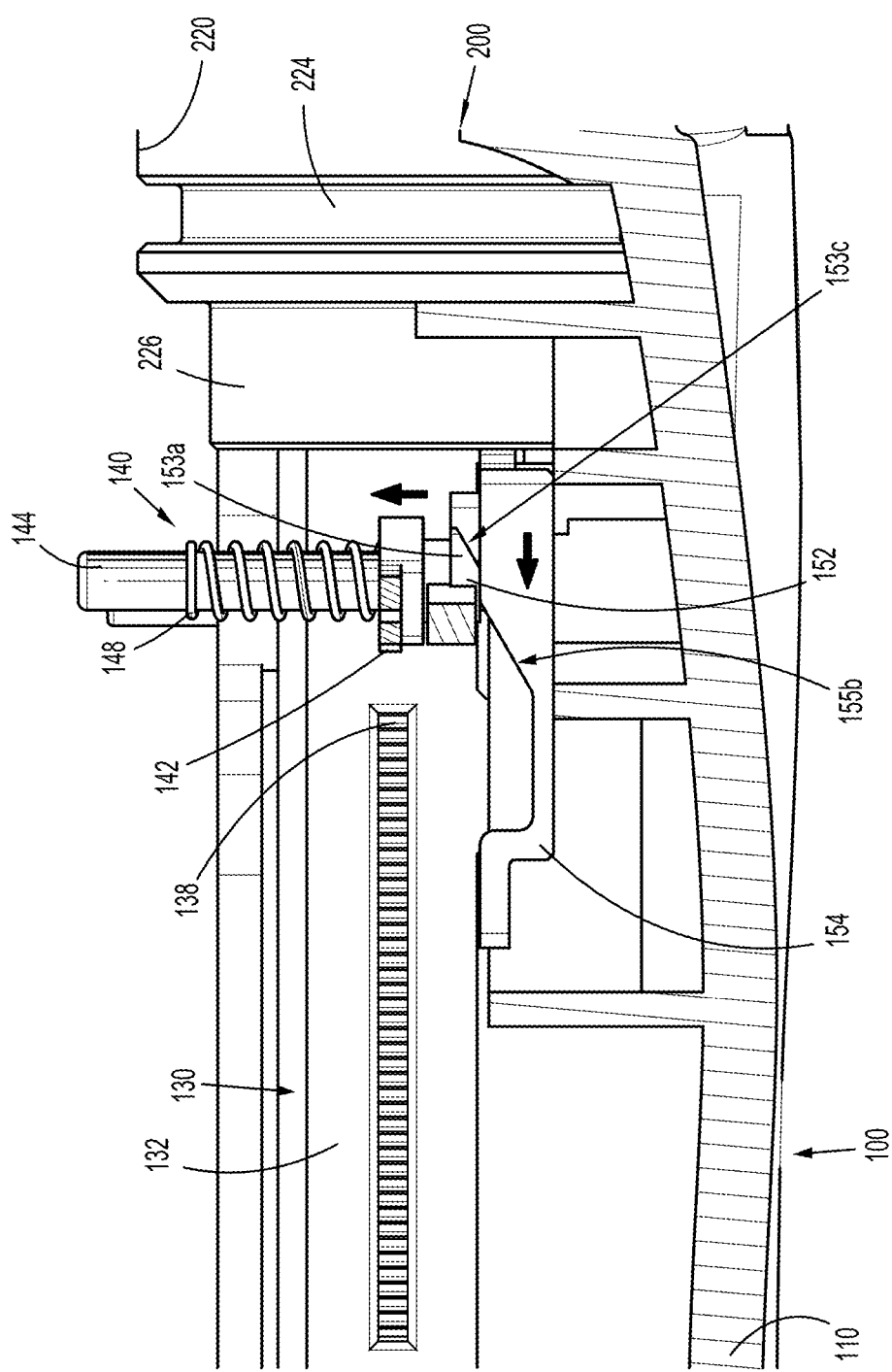
FIG. 12 is an enlarged, bottom, longitudinal, cross-sectional view of a portion of the handle assembly of FIG. 1, with the ratchet mechanism in a ratcheting use condition and the endoscopic assembly of FIGS. 1 and 2 engaged therewith.

With additional reference to FIGS. 11 and 12, upon further proximal sliding of proximal hub 220 into housing 110, drive bar 132 is operably positioned relative to the internal drive assembly (not shown) of endoscopic assembly 200; engagement tooth 168 of latch assembly 160 cams over the proximal end of proximal hub 220 and into engagement within annular channel 224 to engage endoscopic assembly 200 with handle assembly 100; and proximal tube extension 226 of endoscopic assembly 200 urges cam slider 154 proximally such that ratchet pawl 142 is slid transversely from the off-set position (FIG. 9) to the aligned position (FIG. 12). As can be appreciated, in embodiments where the endoscopic assembly utilized with handle assembly 100 is configured for non-ratcheting use, e.g., as with endoscopic assembly 300 (FIGS. 3A and 3B), since the endoscopic assembly is devoid of a proximal tube extension, ratchet pawl 142 remains disposed in the off-set position under the bias of transverse biasing member 148 upon engagement of the non-ratcheting endoscopic assembly with handle assembly 100.

Figure 13:
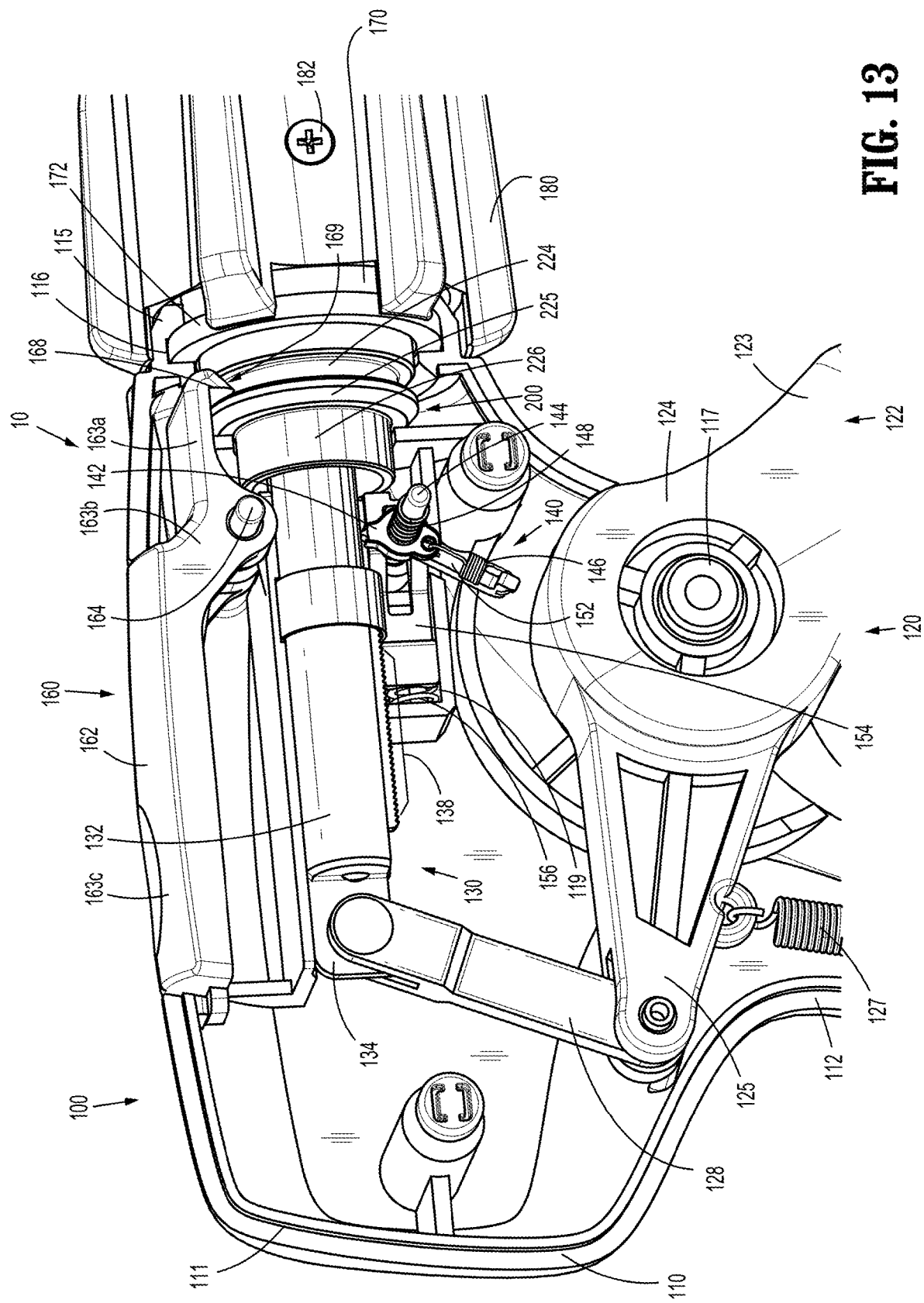
FIG. 13 is a side, perspective view of the endoscopic surgical clip applier of FIG. 1 with a portion of the housing removed to illustrate the internal components therein.

Referring to FIG. 13, with endoscopic assembly 200 engaged with handle assembly 100 and ratchet pawl 142 disposed in the aligned position, in use, grasping portion 123 of trigger 122 is pivoted towards fixed handle portion 112 of housing 110 to urge linkage 128 distally which, in turn, urges drive bar 132 distally through housing 110 and proximal hub 220 to drive the inner drive assembly (not shown) distally. As drive bar 132 is translated distally, ratchet pawl 142 engages ratchet rack 138, inhibiting proximal return of drive bar 132. Thus, trigger 122 may not return towards the un-actuated position and drive bar 132 may not return proximally until a full actuation of trigger 122 has been completed and ratchet pawl 142 has cleared ratchet rack 138. Distal driving of drive bar 132 drives the inner drive assembly (not shown) of endoscopic assembly 200 to fire and form a surgical clip from end effector assembly 360 (FIG. 2A) about tissue. Ratchet mechanism 140, in the ratcheting use condition, enables incremental firing of endoscopic assembly 200, as can be appreciated.

Upon full actuation of trigger 122, e.g., upon reaching the actuated position of trigger 122, ratchet pawl 142 clears and is disengaged from ratchet rack 138, thus permitting trigger 122 to be released and returned to the un-actuated position under the bias of biasing member 127. Thereafter, the above-detailed use may be repeated to fire and form additional surgical clips.

Referring momentarily to FIGS. 1, 2, and 3A-3B, the use of endoscopic assembly 300 with handle assembly 100 is similar to that detailed above with respect to endoscopic assembly 200 except that, with ratchet pawl 142 maintained in the off-set position (due to non-ratcheting endoscopic assemblies not including a proximal tube extension), ratchet pawl 142 is inhibited from engaging ratchet rack 138. Accordingly, during use of endoscopic assembly 300, trigger 122 may be returned towards the un-actuated position and drive bar 132 may be returned proximally at any point during the actuation stroke.

Turning back to FIG. 13, in order to disengage endoscopic assembly 200 from handle assembly 100, e.g., for cleaning and/or sterilization, or to replace endoscopic assembly 200 with another endoscopic assembly, proximal manipulation section 163c of lever latch 162 of latch assembly 160 is depressed inwardly into housing 110, against the bias of biasing member 166, to urge distal engagement section 163a of lever latch 162 out of engagement within annular channel 224 of proximal hub 220 of endoscopic assembly 200. With distal engagement section 163a of lever latch 162 disposed in this disengaged position, proximal hub 220 of endoscopic assembly 200 may be withdrawn distally from handle assembly 100. Upon withdrawal of endoscopic assembly 200 from handle assembly 100, ratchet pawl 142 of ratchet mechanism 140 is returned transversely towards the off-set position under the bias of transverse biasing member 148.

In accordance with the present disclosure, it is contemplated that a surgical system or kit (not shown) may be provided which includes a handle assembly 100, at least one endoscopic assembly 200, at least one endoscopic assembly 300, and instructions for using the same. It is further contemplated that a plurality of handle assemblies may be provided in the surgical system or kit. It is additionally contemplated that the surgical system or kit may include additional endoscopic assemblies, not shown or described herein, which are different from endoscopic assemblies 200 or 300, and which are configured for connection to and operation by handle assembly 100. It is still further contemplated that the surgical system or kit may include at least one cartridge of surgical clips or fasteners (not shown) for use with any of the endoscopic assemblies disclosed herein.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:
1. A surgical clip applying system, comprising:
   a handle assembly, including:
      a housing;
      a trigger pivotably connected to the housing and movable relative thereto between an un-actuated position and an actuated position;
      a drive bar slidably supported within the housing and operably coupled to the trigger such that movement of the trigger from the un-actuated position towards the actuated position translates the drive bar distally through the housing, the drive bar including a ratchet rack disposed thereon; and
      a ratchet mechanism disposed within the housing, the ratchet mechanism including:
         a pawl pin;

a ratchet pawl pivotably and slidably supported on the pawl pin;

a biasing member positioned to bias the ratchet pawl towards an off-set position relative to the ratchet rack, wherein the ratchet pawl is inhibited from operably engaging the ratchet rack upon distal translation of the drive bar;

a cam arm supported on the pawl pin adjacent the ratchet pawl; and a cam slider selectively movable through the housing and relative to the cam arm, the cam slider initially disposed in a first position, wherein the ratchet pawl is maintained in the off-set position under the bias of the biasing member; and a first endoscopic assembly configured for ratcheting use, the first endoscopic assembly including a first proximal hub insertable into and releasably engagable within the housing, wherein, upon insertion of the first proximal hub into the housing, the cam slider is moved from the first position to a second position, wherein the cam slider urges the cam arm along the pawl pin to thereby urge the ratchet pawl along the pawl pin from the off-set position to an aligned position, wherein, in the aligned position, the ratchet pawl is aligned with the ratchet rack to permit operable engagement of the ratchet pawl with the ratchet rack upon distal translation of the drive bar.

2. The clip applying system according to claim 1, further comprising:

a second endoscopic assembly configured for non-ratcheting use, the second endoscopic assembly including a second proximal hub insertable into and releasably engagable within the housing, wherein, upon insertion of the second proximal hub into the handle assembly, the cam slider is maintained in the first position such that the ratchet pawl is maintained in the off-set position under the bias of the biasing member.

3. The clip applying system according to claim 2, wherein the second proximal hub is devoid of a proximal extension such that, upon insertion of the second proximal hub into the housing the cam slider is maintained in the first position and the ratchet pawl is maintained in the off-set position under the bias of the biasing member.

4. The clip applying system according to claim 1, wherein the first proximal hub includes a proximal extension configured to urge the cam slider from the first position to the second position upon insertion of the first proximal hub into the housing.

5. The clip applying system according to claim 1, wherein the handle assembly further comprises a rotation knob extending distally from the housing and rotatably coupled to the housing, the rotation knob and the first proximal hub defining complementary indexing features to rotatably fix the first endoscopic assembly relative to the rotation knob upon insertion of the first proximal hub into the housing.

6. The clip applying system according to claim 1, wherein the handle assembly further comprises a latch assembly operably supported on the housing, the latch assembly including a lever latch configured to releasable engage the first proximal hub upon insertion of the first proximal hub assembly into the housing.

7. The clip applying system according to claim 6, wherein the lever latch includes a distal engagement tooth and wherein the first proximal hub defines an annular channel, the distal engagement tooth configured for engagement within the annular channel upon insertion of the first proximal hub into the housing.

8. The clip applying system according to claim 7, wherein the lever latch includes a proximal manipulation portion configured for manual manipulation to disengage the distal engagement tooth from the annular channel to permit removal of the first proximal hub from the housing.

9. A surgical clip applying system, comprising:

a handle assembly, including:

a housing;

a drive bar configured to translate distally through the housing in response to actuation of the handle assembly, the drive bar including a ratchet rack disposed thereon; and a ratchet mechanism disposed within the housing and including:

a pawl pin;

a ratchet pawl pivotably and slidably supported on the pawl pin;

a biasing member positioned to bias the ratchet pawl towards an off-set position relative to the ratchet rack, wherein the ratchet pawl is inhibited from operably engaging the ratchet rack upon distal translation of the drive bar; and a cam slider longitudinally translatable relative to the housing, the cam slider initially disposed in a first position, wherein the ratchet pawl is maintained in the off-set position under the bias of the biasing member; and a first endoscopic assembly configured for ratcheting use and being insertable into and releasably engagable within the housing, wherein, upon insertion of the first endoscopic assembly into the housing, the cam slider is translated from the first position to a second position, wherein the cam slider urges the ratchet pawl transversely along the pawl pin from the off-set position to an aligned position, wherein, in the aligned position, the ratchet pawl is aligned with the ratchet rack to permit operable engagement of the ratchet pawl with the ratchet rack upon distal translation of the drive bar; and a second endoscopic assembly configured for non-ratcheting use and being insertable into and releasably engagable within the housing, wherein, upon insertion of the second endoscopic assembly into the housing, the cam slider is maintained in the first position such that the ratchet pawl is maintained in the off-set position under the bias of the biasing member.

10. The clip applying system according to claim 9, wherein the handle assembly further comprises a latch assembly operably supported on the housing, the latch assembly including a lever latch configured to releasably engage the first endoscopic assembly or the second endoscopic assembly upon insertion of the first endoscopic assembly or the second endoscopic assembly into the housing.

11. The clip applying system according to claim 9, wherein the first endoscopic assembly includes a first proximal hub defining a proximal extension configured to urge the cam slider from the first position to the second position upon insertion of the first proximal hub into the housing, and wherein the second endoscopic assembly includes a second proximal hub devoid of a proximal extension such that, upon insertion of the second proximal hub into the housing, the cam slider is maintained in the first position.

* * * * *